United States Patent [19]

Bettenhausen et al.

[11] Patent Number: 5,725,097

[45] Date of Patent: Mar. 10, 1998

[54] INSTRUMENT CASSETTE ASSEMBLY

[75] Inventors: Todd E. Bettenhausen; Cary A. Bettenhausen, both of Indianapolis, Ind.

[73] Assignee: Sterilization Cassette Systems, Inc., Greenwood, Ind.

[21] Appl. No.: 738,012

[22] Filed: Oct. 25, 1996

[51] Int. Cl.[6] .................. B65D 45/16; A61L 2/20
[52] U.S. Cl. ............... 206/439; 206/363; 206/1.5; 220/337; 292/210; 422/300
[58] Field of Search ............... 206/363, 364, 206/438, 439, 1.5; 422/300, 310; 292/209, 210; 220/324, 327, 338, 340

[56] References Cited

U.S. PATENT DOCUMENTS

| | | |
|---|---|---|
| 4,541,992 | 9/1985 | Jerge et al. . |
| 4,959,199 | 9/1990 | Brewer . |
| 5,084,251 | 1/1992 | Thomas . |
| 5,098,676 | 3/1992 | Brooks, Jr. ............... 206/438 |
| 5,215,726 | 6/1993 | Kudla et al. ............... 206/370 |
| 5,284,632 | 2/1994 | Kudla et al. . |
| 5,294,413 | 3/1994 | Riihimaki et al. . |
| 5,346,677 | 9/1994 | Risk . |
| 5,490,975 | 2/1996 | Dane ............... 206/438 |
| 5,505,916 | 4/1996 | Berry, Jr. . |
| 5,525,314 | 6/1996 | Hurson ............... 422/300 |

OTHER PUBLICATIONS

Photographs 1–13 of Black & Decker drill bit latch.

Primary Examiner—Paul T. Sewell
Assistant Examiner—Luan K. Bui
Attorney, Agent, or Firm—Maginot, Addison & Moore

[57] ABSTRACT

An instrument cassette and sterile wrap assembly includes a base having an upright sidewall and a horizontal bottom wall, the upright sidewall having a lower slot and an upper aperture defined therein. The assembly includes a latch member having a lower section, an intermediate section and an upper section, wherein (1) the lower section extends through the slot defined in the base, (2) the intermediate section is substantially planar, and (3) the upper section (i) extends through the upper aperture defined in the base, and (ii) has a slot defined therein. The assembly further includes a lid having a horizontal top wall and a tongue member attached thereto, wherein the tongue member extends through the slot defined in the upper section of the latch member when the lid is latched to the base. Moreover, the assembly includes a sterile wrap which envelops the base, the latch member and the lid, wherein the sterile wrap is juxtaposed to the bottom wall of the base, an entire first side of the intermediate portion of the latch member, and the top wall of the lid.

16 Claims, 11 Drawing Sheets

INSTRUMENT CASSETTE ASSEMBLY

BACKGROUND OF THE INVENTION

The present invention relates generally to a cassette used to hold medical or dental instruments, and more particularly, to a cassette used to hold medical or dental instruments which permits the cleaning, sterilization, and storage of such instruments while housed in the cassette.

Medical or dental instruments must be sterilized before they are used. Typically, after each use, the instruments are secured in a holder known as an instrument cassette. Thereafter, the instrument cassette, along with the medical or dental instruments therein, is placed into a cleaning system wherein residual substances from a previous medical or dental procedure are removed from the instruments.

The instrument cassette is subsequently rinsed to remove any residual cleaning solution. After the instrument cassette has dried, the cassette is enveloped with a sterile wrap. The sterile wrap is impermeable to many airborne contaminants and pathogens.

After being wrapped, the instrument cassette is placed in a sterilizing chamber, such as an autoclave, wherein the instrument cassette is subjected to steam at high temperatures in order to eliminate any microbial contamination that may remain on the instruments from their previous use.

After being removed from the sterilizing chamber, the instrument cassette may be stored, with the sterile wrap remaining thereon, until the instruments are next needed. During the storage process, the sterile wrap continues to function as an impermeable barrier between the instruments within the instrument cassette and airborne contaminants and pathogens that may be present in the surrounding environment.

The integrity of the sterile wrap must therefore be maintained in order for it to function properly. For example, if the sterile wrap is torn, an aperture is created through which airborne contaminants and pathogens can reach the instruments within the cassette thus compromising the sterile condition of the instruments.

It is therefore important for the outer surfaces of an instrument cassette to be free of jagged edges and projecting components. One source of jagged edges and projecting components is the latch used to lock the two halves of the cassette together. Often, a portion of the latching mechanism projects abruptly away from the body of the cassette. This creates a surface which can tear the sterile wrap.

The following patents disclose some cassette designs which have been heretofore developed. U.S. Pat. No. 5,505,916 issued to Berry teaches an autoclave cassette 20 with two substantially similar tray halves 21 and 22. A slide portion 24 extends out of the autoclave cassette 20 and receives a retainer portion 25 for the purpose of locking the autoclave cassette.

Moreover, U.S. Pat. No. 5,346,677 issued to Risk teaches an instrument cassette 10 with a lower tray 12 and an upper tray 14. A tab portion 64 extends outwardly from the upper tray 14. The tab portion 64 cooperates with a locking stud 59 to lock the cassette 10.

Further, U.S. Pat. No. 5,284,632 issued to Kudla et al. discloses a cassette 20 with an upper tray 46 and a lower tray 22. A latch plate 66 extends outwardly from the lower tray 22 and receives a latch button 68 to lock the trays 46 and 22 together.

Some of the aforementioned designs include latch mechanisms which contain components that possess edges on which the sterile wrap used to envelop the cassette could be torn. Additionally, some of the aforementioned designs are complex, and are therefore difficult and expensive to manufacture.

What is needed therefore is a medical or dental cassette that is configured to eliminate projecting components which could readily tear the sterile wrap used to envelop the cassette. What is further needed is a medical or dental cassette which is simple and inexpensive to manufacture.

SUMMARY OF THE INVENTION

In accordance with one embodiment of the present invention, there is provided an instrument cassette and sterile wrap assembly. The assembly includes a base having an upright sidewall and a horizontal bottom wall, the upright sidewall having a lower slot and an upper aperture defined therein. The assembly further includes a latch member having a lower section, an intermediate section and an upper section, wherein (1) the lower section extends through the slot defined in the base, (2) the intermediate section is substantially planar, and (3) the upper section (i) extends through the upper aperture defined in the base, and (ii) has a slot defined therein. The assembly also includes a lid having a horizontal top wall and a tongue member attached thereto, wherein the tongue member extends through the slot defined in the upper section of the latch member when the lid is latched to the base. Further, the assembly includes a sterile wrap which envelops the base, the latch member and the lid, wherein the sterile wrap is juxtaposed to the bottom wall of the base, an entire first side of the intermediate portion of the latch member, and the top wall of the lid.

Pursuant to another embodiment of the invention, there is provided a method of protecting an instrument cassette having a lid, a base and a latch member. The method includes, firstly, latching the lid to the base with the latch member, wherein (1) the base has a horizontal bottom wall, (2) the lid has a horizontal top wall and a tongue member attached thereto, and (3) the latch member includes (i) a lower section fixed in position relative to the base, (ii) a planar intermediate section, and (iii) an upper section which cooperates with the tongue member of the lid to latch the lid to the base, and secondly, wrapping the lid, the base and the latch member with a sterile wrap so that the sterile wrap is juxtaposed to the bottom wall of the base, an entire first side of the intermediate portion, and the top wall of the lid.

In accordance with yet another embodiment of the invention, there is provided an instrument cassette. The cassette includes a base having an upright sidewall and a horizontal bottom wall, the upright sidewall having a lower slot and an upper aperture defined therein. The cassette further includes a latch member having a lower section, an intermediate section and an upper section, wherein (1) the lower section extends through the slot defined in the base, (2) the intermediate section is substantially planar, and (3) the upper section (i) extends through the upper aperture defined in the base, and (ii) has a slot defined therein. The cassette additionally includes a lid having a horizontal top wall and a tongue member attached thereto, wherein the tongue member extends through the slot defined in the upper section of the latch member when the lid is latched to the base.

Pursuant to still another embodiment of the invention, there is provided an instrument cassette. The cassette includes a base having a bottom wall and an upright sidewall, and a lid having a tongue member. The assembly further includes a latch member having (i) a lower section fixed in position relative to the base, (ii) an intermediate section, and (iii) an upper section which cooperates with the tongue member of the lid to latch the lid to the base, wherein the intermediate portion of the latch member is movable between a latch position and a release position, wherein one side of the intermediate section of the latch member is juxtaposed to the upright sidewall of the base when the intermediate section is located in the release position, and wherein the one side of the intermediate portion of the latch member is spaced apart from the upright sidewall of the base when the intermediate section is located in the latch position.

It is therefore an object of this invention to provide a new and useful instrument cassette assembly.

It is a further object of this invention to provide an improved instrument cassette assembly.

It is further an object of this invention to provide a new and useful instrument cassette.

It is further an object of this invention to provide an improved instrument cassette.

It is further an object of this invention to provide a new and useful method of protecting an instrument cassette.

It is further an object of this invention to provide an improved method of protecting an instrument cassette.

It is a further object of this invention to provide an instrument cassette that is configured to eliminate projecting components which could readily tear the sterile wrap used to envelop the cassette.

It is a further object of this invention to provide an instrument cassette which is easily manufactured and has a latch which uses only a single moving component.

The above and other objects, features, and advantages of the present invention will become apparent from the following description and the attached drawings.

DETAILED DESCRIPTION OF THE INVENTION

While the invention is susceptible to various modifications and alternative forms, a specific embodiment thereof has been demonstrated by way of example in the drawings and will herein be described in detail. It should be understood that there is no intent to limit the invention to the particular form disclosed, but on the contrary, the intention is to cover all modifications, equivalents, and alternatives falling within the spirit and scope of the invention as defined by the appended claims.

Figure 1:
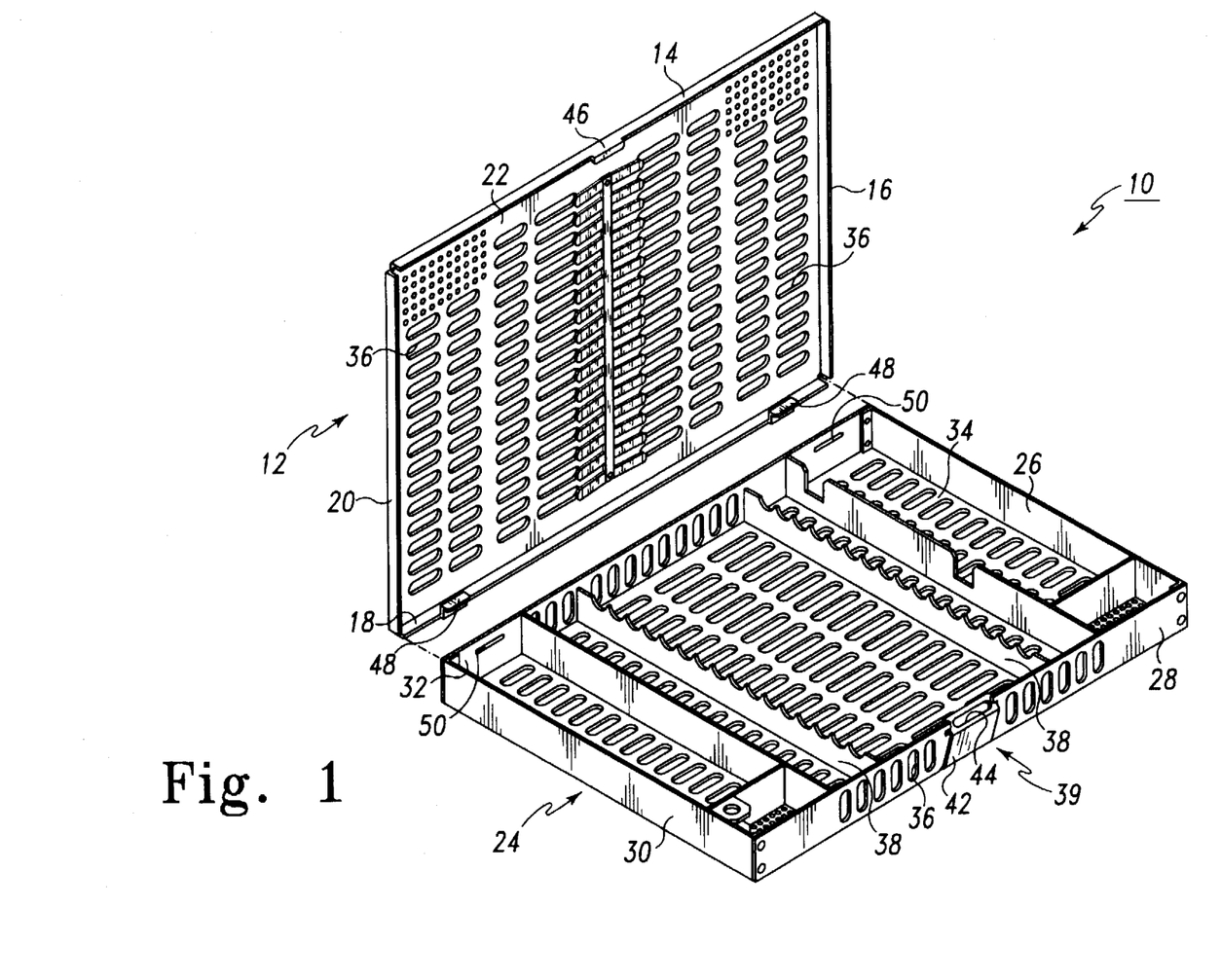
FIG. 1 is a perspective view of an instrument cassette which incorporates the features of the present invention therein.

Referring now to FIG. 1, there is shown an instrument cassette 10. The cassette 10 is used to hold medical or dental instruments and permits cleaning, sterilization, and storage of such instruments while housed in the cassette 10.

The instrument cassette 10 includes a lid 12 and a base 24. The lid 12 includes a top wall 22. A plurality of side walls 14, 16, 18, and 20 are attached in substantially perpendicular fashion to the periphery of the top wall 22. Collectively, the side walls 14, 16, 18, and 20 cooperate with the top wall 22 to provide a tray-like structure as shown in FIG. 1.

Similarly, the base 24 includes a bottom wall 34. A plurality of side walls 26, 28, 30, and 32 are attached in substantially perpendicular fashion to the periphery of the bottom wall 34. Collectively, the side walls 26, 28, 30, and 32 cooperate with the bottom wall 34 to provide a tray-like structure as shown in FIG. 1.

A plurality of holes 36 are defined in each of the top wall 22, the bottom wall 34, the side wall 28, and the side wall 32. The holes 36 are provided in a number of different sizes. It should be appreciated that the holes 36 could be added to, or deleted from, any of the walls of the lid 12 or the base 24 to meet the needs of a particular instrument cassette 10.

A pair of hinge members 48 is disposed on the side wall 18 of the lid 12. The hinge members 48 are received into a pair of hinge slots 50 defined in the side wall 32. The hinge members 48 cooperate with the hinge slots 50 to allow the lid 12 to pivot relative to the base 24. The hinge members 48 are shown integrated into the side wall 18, but it should be appreciated that the hinge members 48 could be separate components mechanically fastened to the side wall 18.

A pair of instrument racks 38 are disposed perpendicular to the bottom wall 34. The instrument racks 38 hold medical or dental instruments (not shown) during the cleaning and sterilization process, and the subsequent storage period until the instruments are next used.

The instrument cassette 10 includes a latch assembly 39. The latch assembly 39 includes a latch member 42 which is shown in more detail in FIGS. 2 and 3. A slot 44 is defined in the latch member 42 and cooperates with a tongue 46 of the lid 12. When the tongue 46 is received in the slot 44, the lid 12 is latched to the base 24, thereby securing the instruments within the cassette 10.

The components of the cassette 10 are made from stainless steel, or similar material. For example, the latch member 42 may be made from half-hard grade stainless steel 302. Also, the lid 12 and base 24 may be made from stainless steel 304.

Figure 2:
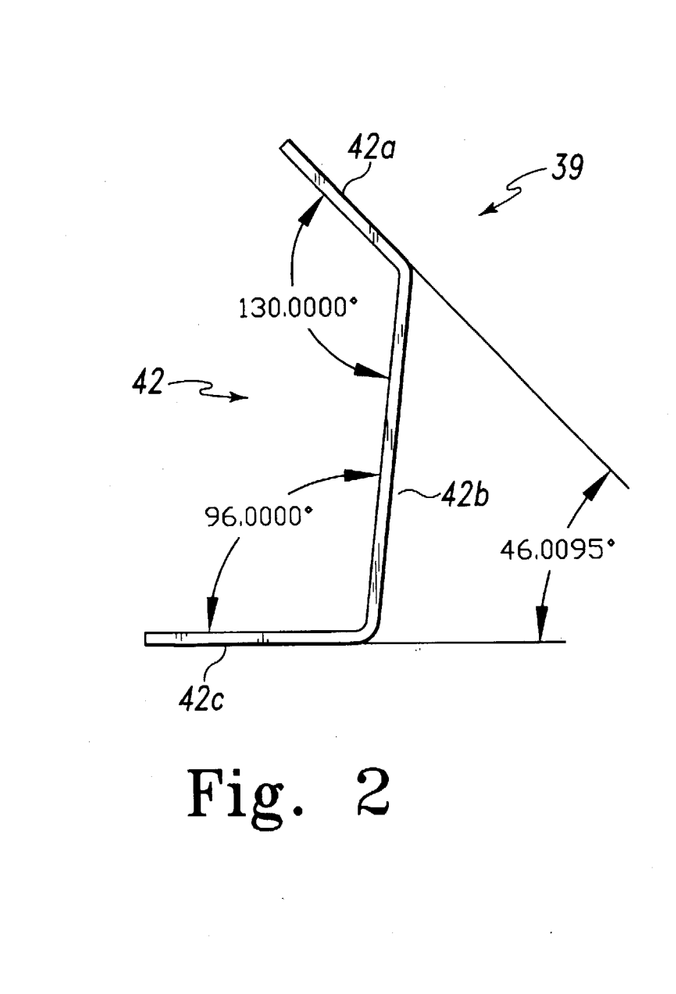
FIG. 2 is a side elevational view of the latch member of the instrument cassette of FIG. 1.
Figure 3:
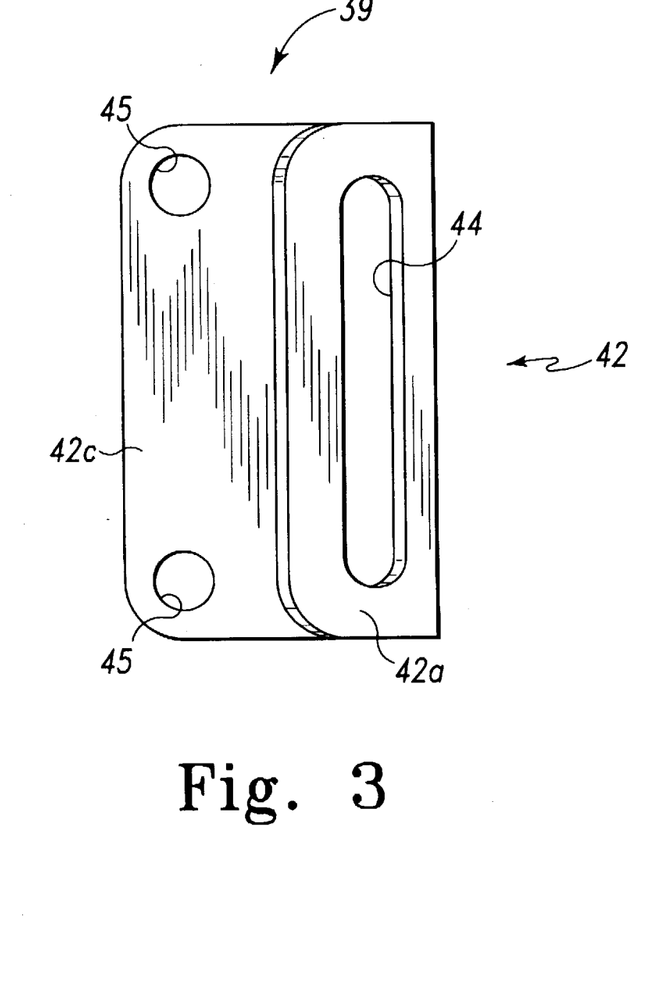
FIG. 3 is a top elevational view of the latch member of the instrument cassette of FIG. 1.

A shown in FIGS. 2 and 3, the latch member 42 includes a latch section 42a, a latch section 42b, and a latch section 42c. The latch section 42c and the latch section 42b form an angle which is approximately 96°. Moreover, the latch section 42a and the latch section 42b form an angle which is approximately 130°. The slot 44 is provided in the latch section 42a in order to receive the tongue 46 (see FIG. 1) of the lid 12. A pair of holes 45 is defined in the latch section 42c. The holes 45 receive rivets to secure the latch member 42 to the bottom wall 34 of the base 24.

The latch member 42 is constructed from a single piece of material. The latch member 42 requires only two bends, a slot, and two holes, and thus is relatively simple and inexpensive to manufacture.

Figure 4:
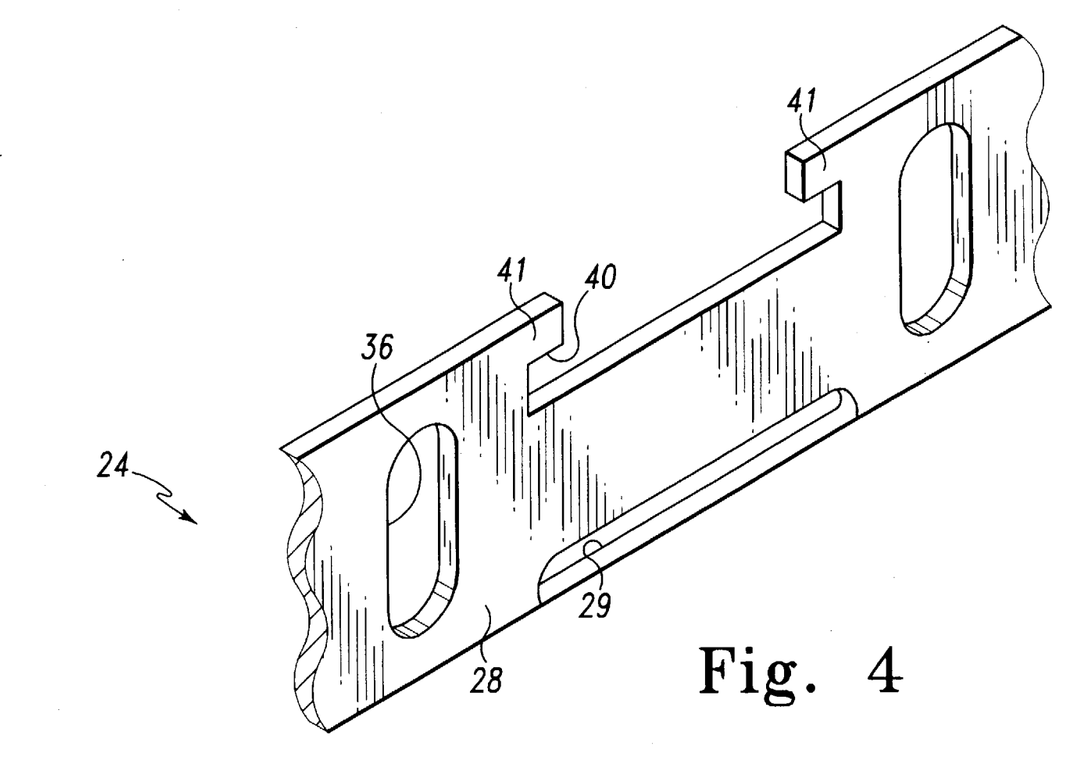
FIG. 4 is a fragmentary perspective view of the base of the instrument cassette of FIG. 1.

FIG. 4 is a fragmentary perspective view of the base 24 of the cassette 10. The base 24 includes the side wall 28 which has an aperture 40 defined therein. Disposed on each end of the aperture 40 is a flange 41. The side wall 28 includes a slot 29 defined therein which is located below the aperture 40. After assembly of the cassette 10, the latch member 42 extends through the slot 29 as shown in FIGS. 5, 9-12.

Figure 5:
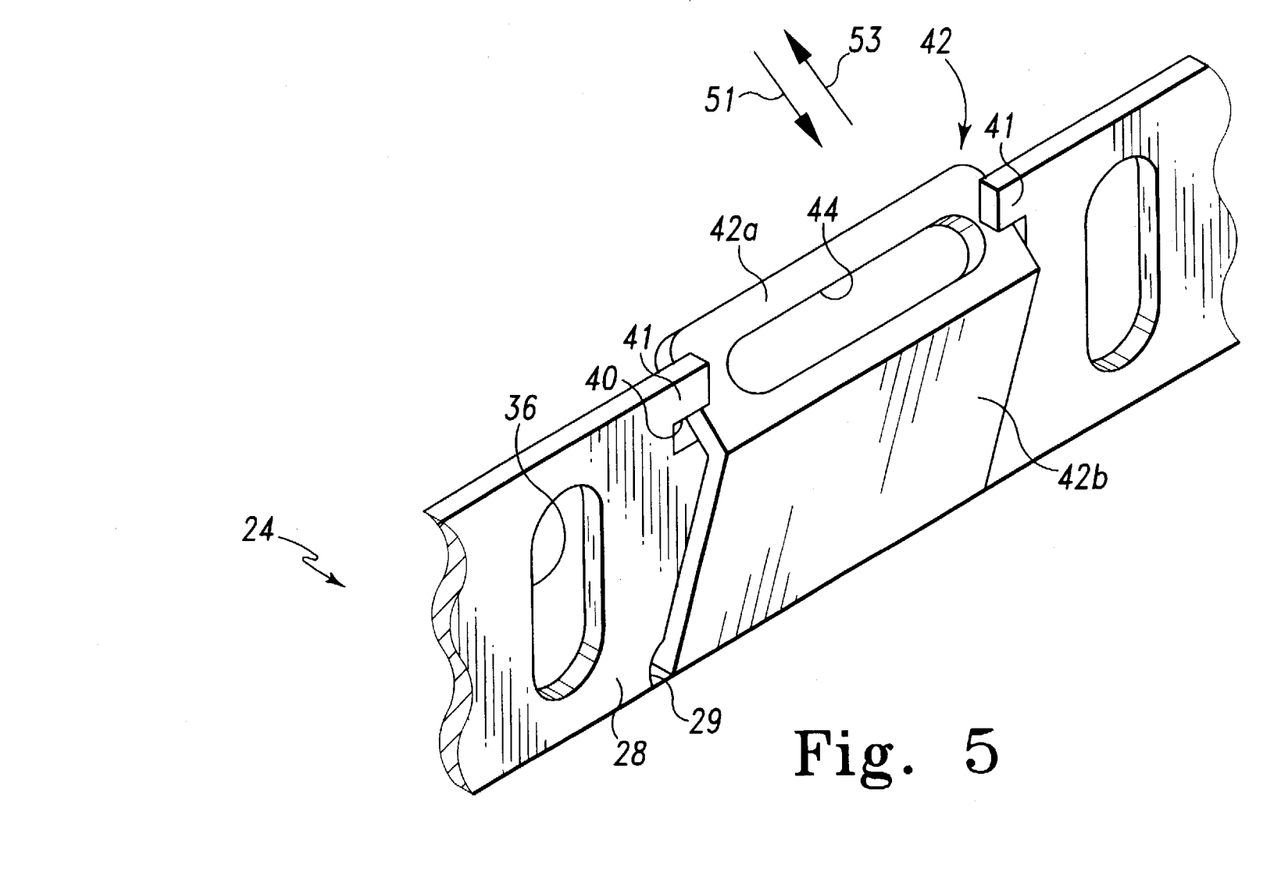
FIG. 5 is a fragmentary perspective view showing the relationship between the base of FIG. 4 and the latch member of FIG. 2.
Figure 6:
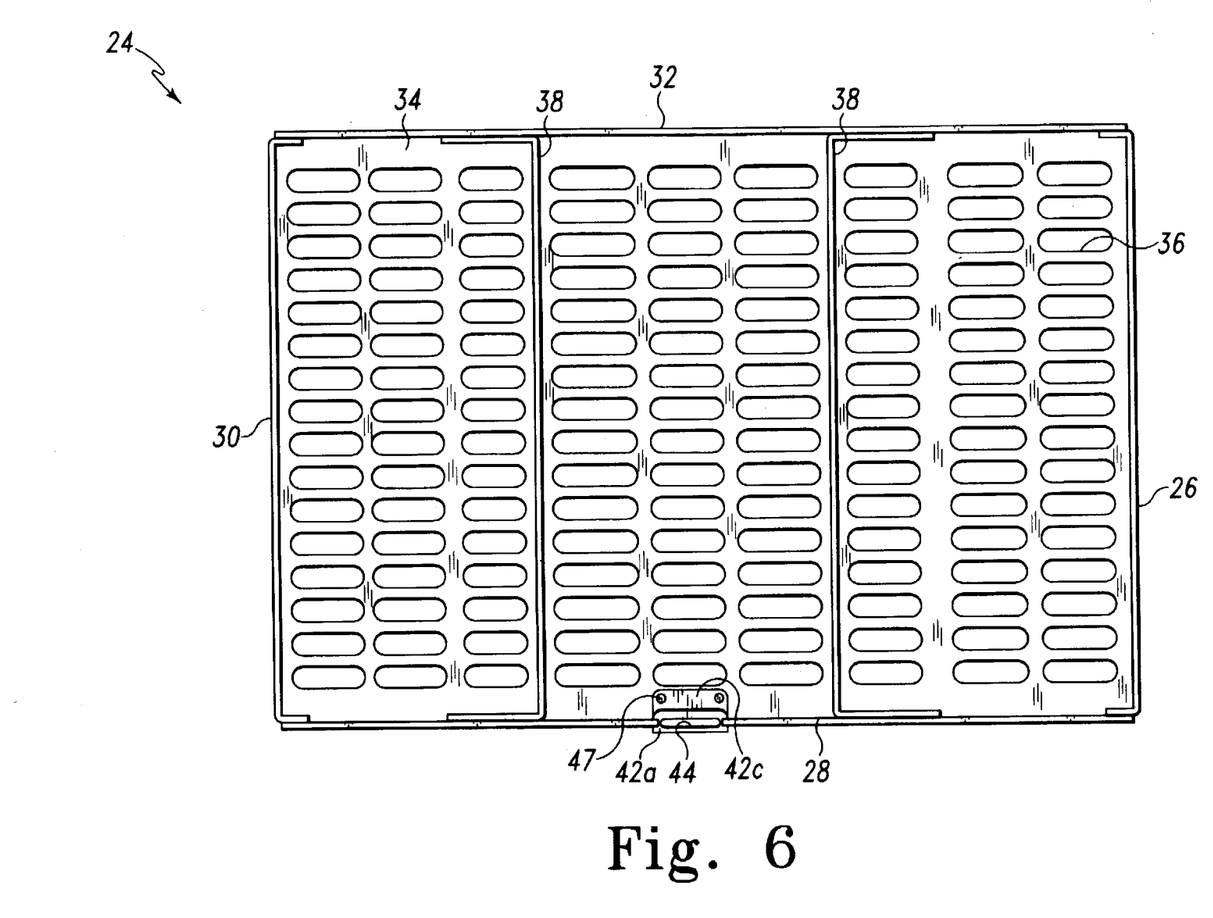
FIG. 6 is a top elevational view of the base of the instrument cassette of FIG. 1.

FIG. 5 is a fragmentary perspective view which shows the relationship between the base 24 and the latch member 42. FIG. 6 is a top elevational view of the base 24 of the cassette 10. The latch section 42c is disposed on the bottom wall 34 having been received through the slot 29. The latch section 42c is fastened to the bottom wall 34 with rivets 47. The rivets 47 are located with adequate clearance from the side 28 and the latch section 42a such that they are easily accessible with a drill for the purpose of removing the rivets 47 and replacing the latch member 42 should the need arise.

Referring again to FIG. 5, the latch section 42a extends through the aperture 40. The latch section 42a is resiliently biased against the flanges 41 in the direction as indicated by arrow 51 as shown in FIG. 5. Moreover, the side wall 28 prevents damage to the latch member 42 by preventing the latch member from being over extended in the direction indicated by arrow 53. In particular, as the latch member is being moved in the direction of arrow 53, the sidewall 28 functions as a stop to prevent further movement of the latch member at a predetermined point in its path of travel.

Figure 7:
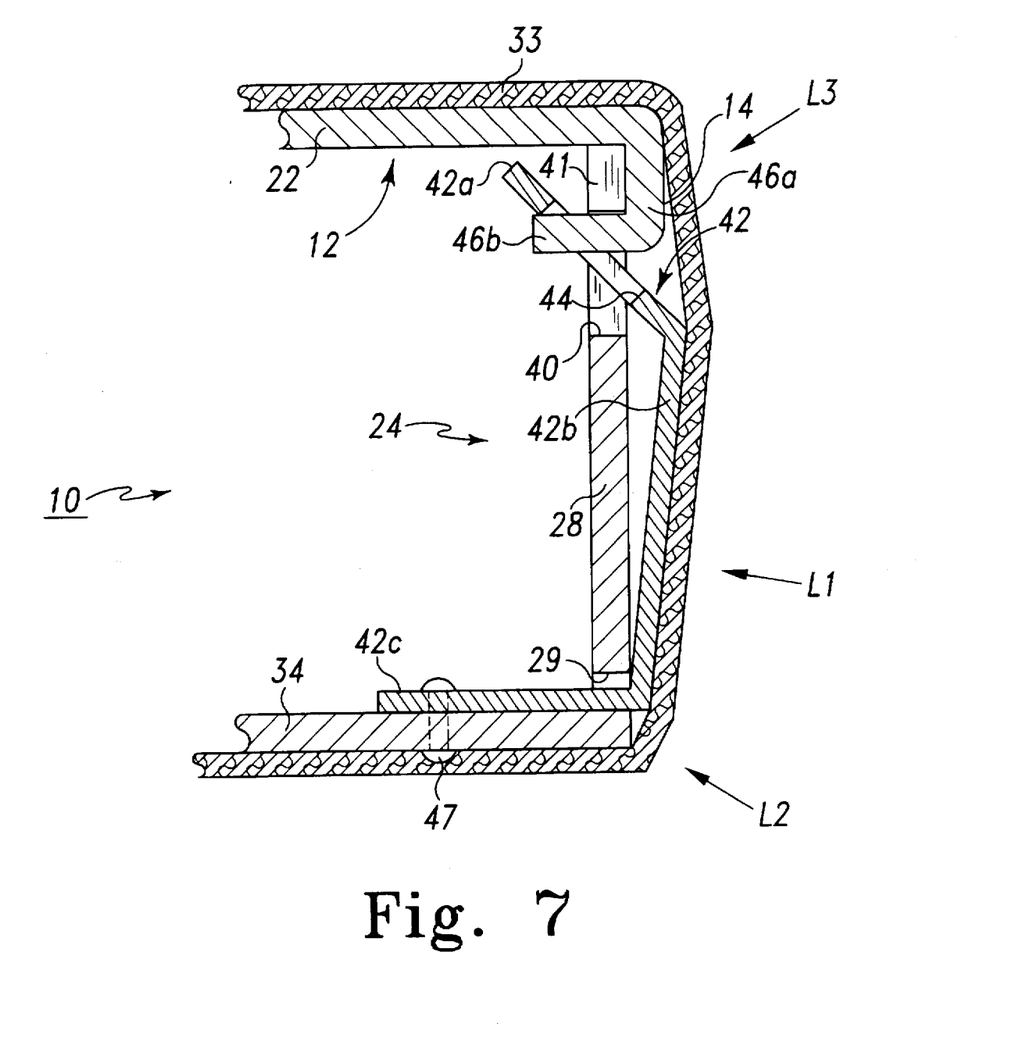
FIG. 7 is a fragmentary cross sectional view of the instrument cassette of FIG. 1 enveloped in a sterile wrap.

FIG. 7 is a fragmentary cross sectional view of the cassette 10 shown wrapped in a sterile wrap 33. The cassette 10 is maintained in this wrapped condition during sterilization of the cassette 10 and further during storage of the cassette until the instruments contained therein are needed for the next medical or dental procedure. During this storage period, the wrapped cassette 10 may be subjected to external forces which are generally normal to the storage of any item. For example, when the wrapped cassette 10 is stored on a shelve of a shelving unit, objects may bump the wrapped cassette. In addition, the wrapped cassette may be handled whereby the fingers of a nurse or doctor may grasp the wrapped cassette thus applying external forces to the sterile wrap 33 in the direction of the cassette 10. These types of external forces have a tendency to cause the sterile wrap 33 to tear or rip thus negatively affecting the sterile condition of the instruments contained in the wrapped cassette 10.

It is important to note that the configuration defined by the latch member 42, the base 24 and the lid 12 has substantial advantages in maintaining the integrity of the sterile wrap 33 which envelopes the cassette 10. In particular, when the lid 12 is locked to the base 24, the latch section 42b provides a planar surface against which the sterile wrap 33 abuts (see Location L1). At a location L2, the sterile wrap 33 transitions from the bottom wall 34 of base 24 to a lower end of the latch section 42b without encountering abrupt edges. Moreover, at a location L3, the sterile wrap transitions from an upper end of latch section 42b to the top wall 22 of lid 12 additionally without encountering abrupt edges.

Thus, the configuration defined by the latch member 42, the base 24 and the lid 12 reduces the likelihood that the sterile wrap 33 would be torn during storage and handling of the wrapped cassette.

Figure 8:
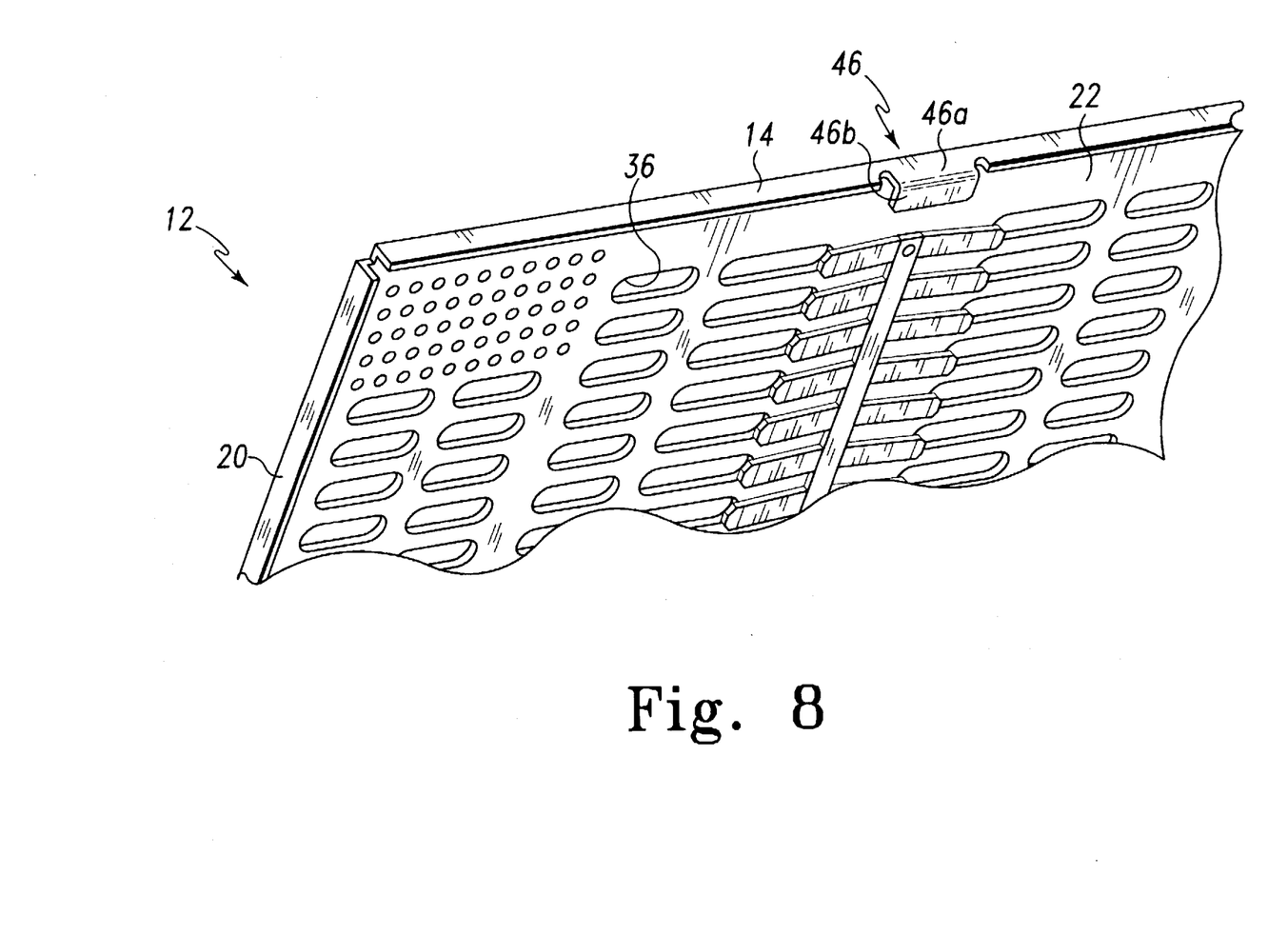
FIG. 8 is a fragmentary perspective view of the lid of the instrument cassette of FIG. 1.

Referring now to FIG. 8, a fragmentary perspective view of the lid 12 is shown. The lid 12 includes the side wall 14 which is affixed in a substantially perpendicular fashion to the top wall 22.

Disposed on the side wall 14 is the tongue 46. The tongue 46 is shown integrated into the side wall 14, but it should be appreciated that the tongue 46 could be a separate component mechanically fastened to the side wall 14.

The tongue 46 includes a tongue section 46a and a tongue section 46b. The tongue section 46a extends directly from the side wall 14 in a downward direction as shown in FIGS. 9-12. The tongue section 46b extends from the tongue section 46a in an inward direction towards the center of the cassette 10 (see also FIGS. 9-12).

Figure 9:
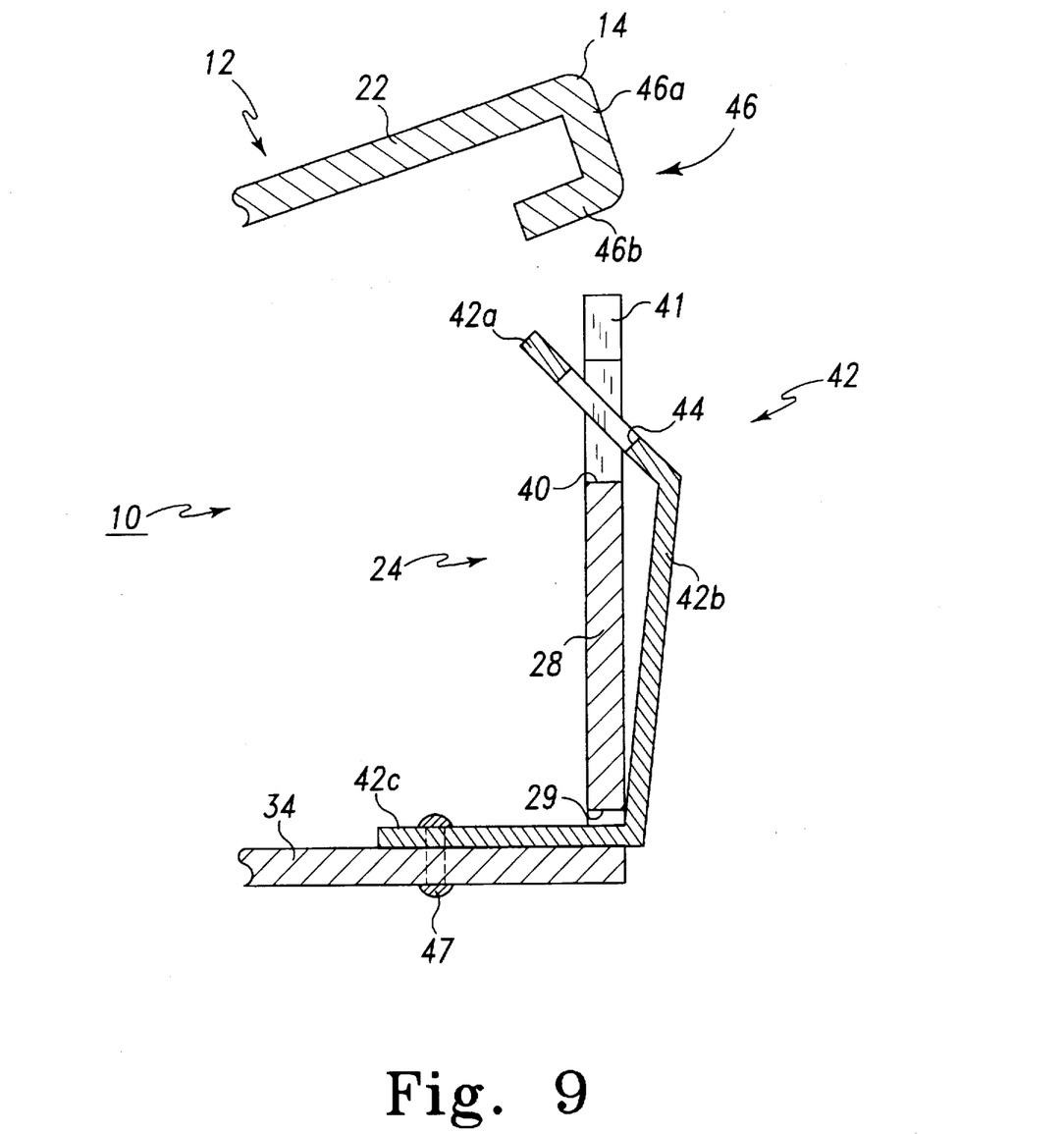
FIGS. 9–11 are fragmentary cross sectional views of the instrument cassette showing successive steps during the process of latching the lid to the base.
Figure 10:
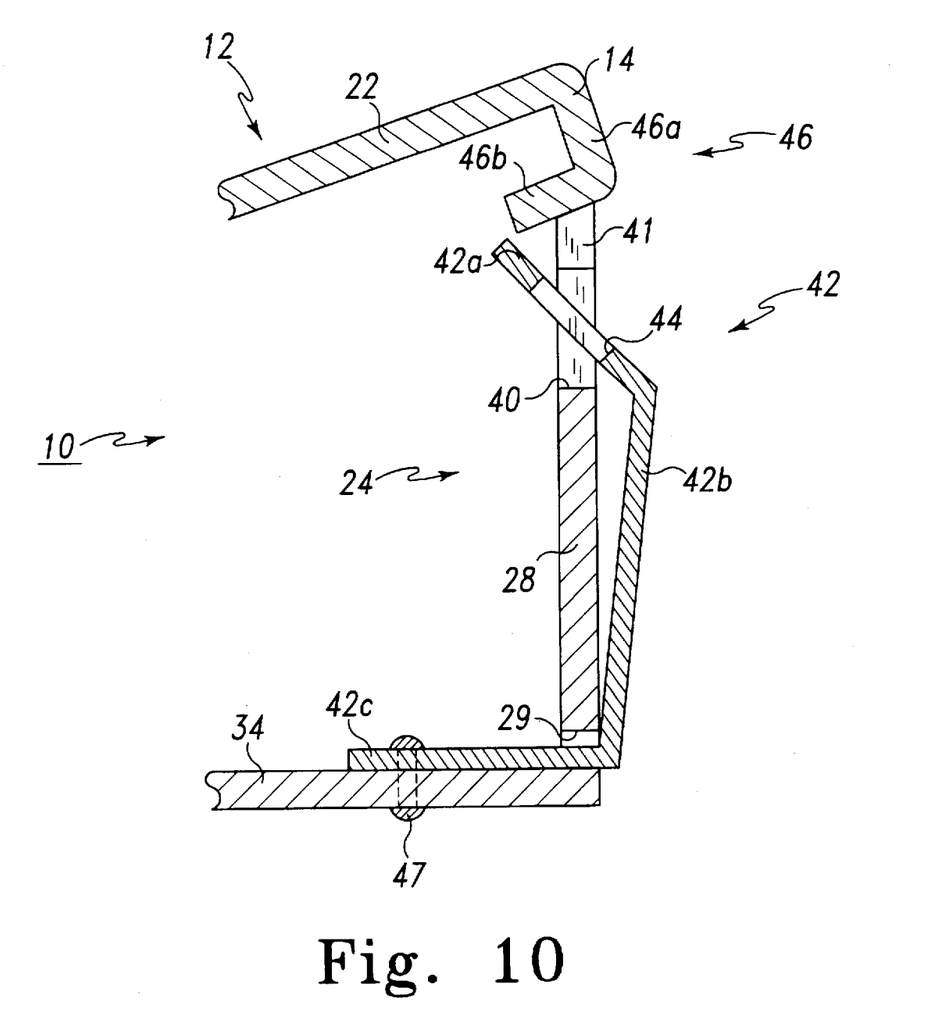
Figure 11:
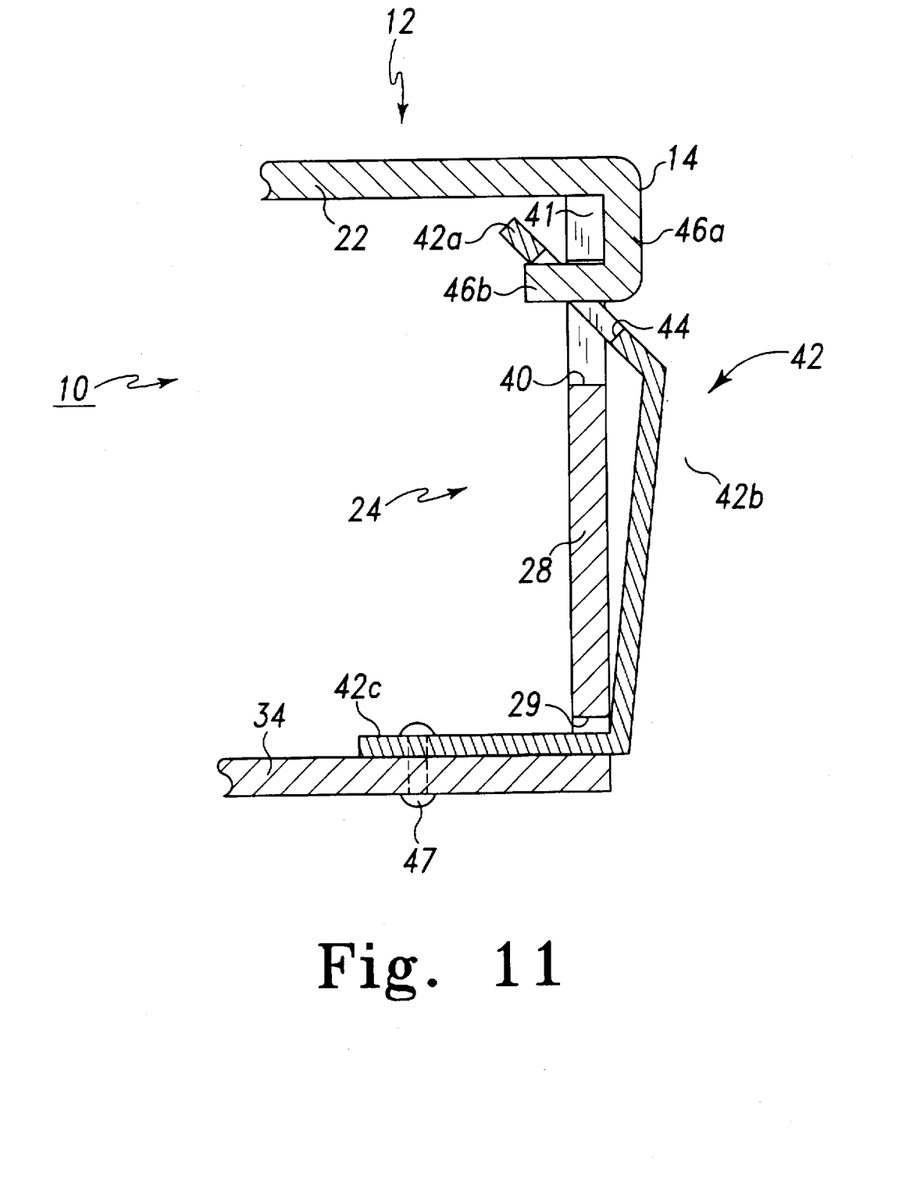

FIGS. 9-11 show the instrument cassette 10 during the sequential steps of the latching process. In particular, the tongue section 46b is moved downward and into contact with the latch section 42a. Once in contact with the tongue section 42a, further downward forces are applied to the tongue section 46b. When these downward forces of the tongue section 46b become greater than the biasing forces inherent in the latch member 42, the latch section 42a is moved inwardly. As the latch section 42a is moved inwardly, the angled surface thereof directs the slot 44 toward the tongue section 46b. As the tongue section 46b is continued to be forced downwardly, the tongue section 46b is advanced into the slot 44 and the latch member 42 springs back to a latch position to complete the latching process as shown in FIG. 11. This effectively latches the lid 12 to the base 24.

The length of the tongue section 46b is designed to reduce the distance the tongue section 46b intrudes into the interior of the cassette 10. This allows for more usable space within the instrument cassette 10.

Figure 12:
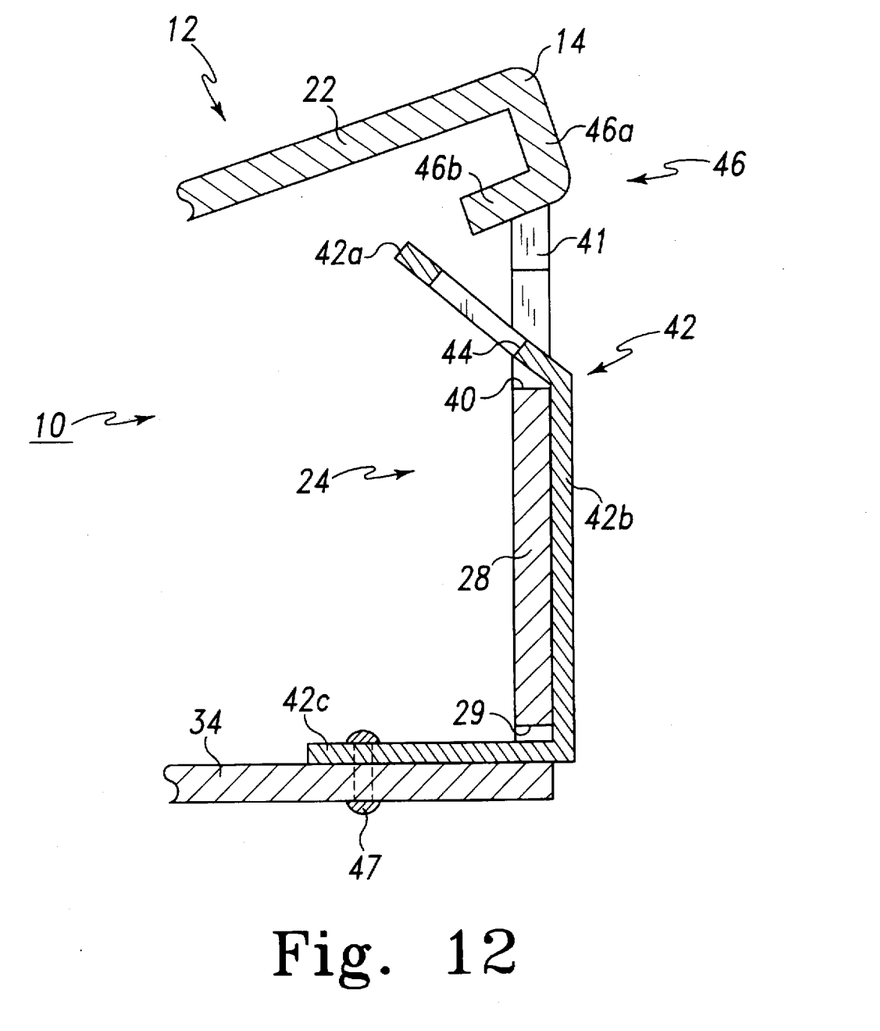
FIG. 12 is a fragmentary cross sectional view of the instrument cassette showing the latch member positioned in the release position.

In order for the lid 12 to be unlatched from the base 24, the latch section 42b is pushed inwardly to a release position as shown in FIG. 12. As the latch member 42 is being advanced to the release position, the tongue section 46b is allowed to be raised upwardly through the slot 44. The lid 12 can then be lifted away from the base 24, thereby allowing access to the instruments within the cassette 10.

Once the tongue section 46b has been removed from the slot 44, the latch member 42 returns to its original position as shown in FIG. 9. No other manipulations need be performed on the latch member 42 prior to reinitiating the latching steps. This feature removes some extra steps often associated with other types of latches and thereby simplifies the use of the cassette 10. By contrast, the catch in a draw latch must be slid back to its initial position after each use.

As described in the aforementioned steps of the latching process, the latch member 42 is the only moving component of the latch assembly 39. This not only simplifies the design, but also increases the reliability of the cassette 10. In addition, as described above in reference to FIG. 6, should the latch member 42 wear beyond usefulness, it can easily be replaced.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected. For example, while the latch section 42c of the latch member 42 is shown attached to the bottom wall 34 of the base 24, it is also contemplated that the latch member 42 may be alternatively configured such that the latch section 42c is attached to the sidewall 28 of the base 24 instead of the bottom wall 34 of the base 24.

What is claimed is:

1. An instrument cassette and sterile wrap assembly, comprising:

a base having an upright sidewall and a horizontal bottom wall, said upright sidewall having a lower slot and an upper aperture defined therein;

a latch member having a lower section, an intermediate section and an upper section, wherein (1) said lower section extends through said slot defined in said base, (2) said intermediate section is substantially planar, and (3) said upper section (i) extends through said upper aperture defined in said base, and (ii) has a slot defined therein;

a lid having a horizontal top wall and a tongue member attached thereto, wherein said tongue member extends through said slot defined in said upper section of said latch member when said lid is latched to said base; and a sterile wrap which envelops said base, said latch member and said lid, wherein said sterile wrap is juxtaposed to said bottom wall of said base, an entire first side of said intermediate section of said latch member, and said top wall of said lid.

2. The assembly of claim 1, wherein:

said lower section of said latch member is substantially planar and includes a first hole defined therein, said bottom wall of said base is substantially planar and includes a second hole defined therein, said lower section of said latch member is juxtaposed to said bottom wall of said base, and said first hole is aligned with said second hole.

3. The assembly of claim 2, further comprising a rivet located in said first hole and said second hole, wherein said rivet is spaced apart from said upright sidewall of said base.

4. The apparatus of claim 1, wherein:

said intermediate section of said latch member is movable between a release position and a latch position, a second side of said intermediate portion is juxtaposed to said upright sidewall of said base when said intermediate portion of said latch member is positioned in said release position.

5. The apparatus of claim 4, wherein said tongue member of said lid is positioned within said slot of said upper section of said latch member when said latch member is positioned in said latch position.

6. The apparatus of claim 1, wherein:

said lower section of said latch member is connected to said intermediate section of said latch member so as to define an angle having a value between approximately 90°–100°, and said intermediate section of said latch member is connected to said upper section of said latch member so as to define an angle having a value between approximately 125°–135°.

7. An instrument cassette, comprising:

a base having an upright sidewall and a horizontal bottom wall, said upright sidewall having a lower slot and an upper aperture defined therein;

a latch member having a lower section, an intermediate section and an upper section, wherein (1) said lower section extends through said slot defined in said base, (2) said intermediate section is substantially planar, and (3) said upper section (i) extends through said upper aperture defined in said base, and (ii) has a slot defined therein; and a lid having a horizontal top wall and a tongue member attached thereto, wherein said tongue member extends through said slot defined in said upper section of said latch member when said lid is latched to said base.

8. The assembly of claim 7, wherein:

said lower section of said latch member is substantially planar and includes a first hole defined therein, said bottom wall of said base is substantially planar and includes a second hole defined therein, said lower section of said latch member is juxtaposed to said bottom wall of said base, and said first hole is aligned with said second hole.

9. The assembly of claim 8, further comprising a rivet located in said first hole and said second hole, wherein said rivet is spaced apart from said upright sidewall of said base.

10. The apparatus of claim 7, wherein:

said intermediate section of said latch member is movable between a release position and a latch position, a second side of said intermediate portion is juxtaposed to said upright sidewall of said base when said intermediate portion of said latch member is positioned in said release position.

11. The apparatus of claim 10, wherein said tongue member of said lid is positioned within said slot of said upper section of said latch member when said latch member is positioned in said latch position.

12. The apparatus of claim 7, wherein:

said lower section of said latch member is connected to said intermediate section of said latch member so as to define an angle having a value between approximately 90°–100°, and said intermediate section of said latch member is connected to said upper section of said latch member so as to define an angle having a value between approximately 125°–135°.

13. An instrument cassette, comprising:

a base having a bottom wall and an upright sidewall;

a lid having a tongue member;

a latch member having (i) a lower section fixed in position relative to said base, (ii) an intermediate section, and (iii) an upper section which cooperates with said tongue member of said lid to latch the lid to the base, wherein said intermediate portion of said latch member is movable between a latch position and a release position, wherein one side of said intermediate section of said latch member is juxtaposed to said upright sidewall of said base when said intermediate section is located in the release position, wherein said one side of said intermediate section of said latch member is spaced apart from said upright sidewall of said base when said intermediate section is located in the latch position, wherein said lower section of said latch member is substantially planar and includes a first hole defined therein, and wherein said bottom wall of said base is substantially planar and includes a second hole defined therein, wherein said lower section of said latch member is juxtaposed to said bottom wall of said base, and wherein said first hole is aligned with said second hole.

14. The assembly of claim 13, further comprising a rivet located in said first hole and said second hole, wherein:

said rivet is spaced apart from said upright sidewall of said base.

15. An instrument cassette, comprising:

a base having a bottom wall and an upright sidewall;

a lid having a tongue member;

a latch member having (i) a lower section fixed in position relative to said base, (ii) an intermediate section, and (iii) an upper section which cooperates with said tongue member of said lid to latch the lid to the base, wherein said intermediate portion of said latch member is movable between a latch position and a release position, wherein one side of said intermediate section of said latch member is juxtaposed to said upright sidewall of said base when said intermediate section is located in the release position, wherein said one side of said intermediate section of said latch member is spaced apart from said upright sidewall of said base when said intermediate section is located in the latch position, wherein said upper section of said latch member has a slot defined therein, and wherein said tongue member of said lid is positioned within said slot of said upper section of said latch member when said intermediate section of said latch member is positioned in said latch position.

16. An instrument cassette, comprising:

a base having a bottom wall and an upright sidewall;

a lid having a tongue member;

a latch member having (i) a lower section fixed in position relative to said base, (ii) an intermediate section, and (iii) an upper section which cooperates with said tongue member of said lid to latch the lid to the base, wherein said intermediate portion of said latch member is movable between a latch position and a release position, wherein one side of said intermediate section of said latch member is juxtaposed to said upright sidewall of said base when said intermediate section is located in the release position, wherein said one side of said intermediate section of said latch member is spaced apart from said upright sidewall of said base when said intermediate section is located in the latch position, wherein said lower section of said latch member is connected to said intermediate section of said latch member so as to define an angle having a value between approximately 90°–100°, and wherein said intermediate section of said latch member is connected to said upper section of said latch member so as to define an angle having a value between approximately 125°–135°.

* * * * *